(12) United States Patent
Chon

(10) Patent No.: US 10,058,365 B2
(45) Date of Patent: Aug. 28, 2018

(54) PROTECTOR

(71) Applicant: Jae-Hyung Chon, Rancho Palos Verdes, CA (US)

(72) Inventor: Jae-Hyung Chon, Rancho Palos Verdes, CA (US)

( * ) Notice: Subject to any disclaimer, the term of this patent is extended or adjusted under 35 U.S.C. 154(b) by 5 days.

(21) Appl. No.: 15/122,097

(22) PCT Filed: May 23, 2014

(86) PCT No.: PCT/KR2014/004598
§ 371 (c)(1),
(2) Date: Aug. 26, 2016

(87) PCT Pub. No.: WO2015/129960
PCT Pub. Date: Sep. 3, 2015

(65) Prior Publication Data
US 2017/0065318 A1 Mar. 9, 2017

(30) Foreign Application Priority Data
Feb. 26, 2014 (KR) .................. 10-2014-0022488

(51) Int. Cl.
*A61B 17/84* (2006.01)
*A61L 31/04* (2006.01)
(Continued)

(52) U.S. Cl.
CPC .............. *A61B 17/842* (2013.01); *A61F 2/08* (2013.01); *A61L 31/04* (2013.01); *A61L 31/14* (2013.01); *A61B 17/68* (2013.01); *A61B 17/8615* (2013.01); *A61B 17/8625* (2013.01); *A61F 2/0063* (2013.01); *A61F 2002/0858* (2013.01); *A61F 2002/0888* (2013.01)

(58) Field of Classification Search
CPC ..... A61B 17/842; A61B 17/8615; A61F 2/08; A61L 31/14; A61L 31/04
See application file for complete search history.

(56) References Cited

U.S. PATENT DOCUMENTS 3,545,008 A * 12/1970 Bader, Jr. .................. A61F 2/08
128/DIG. 21
2002/0177853 A1 11/2002 Chervitz et al.
(Continued)

FOREIGN PATENT DOCUMENTS

KR 1020070019996 2/2007
WO 2005037150 4/2005
(Continued)

OTHER PUBLICATIONS

International Search Report for related international application No. PCT/KR2014/004598 dated Nov. 20, 2014.
(Continued)

*Primary Examiner* — Christian Sevilla
(74) *Attorney, Agent, or Firm* — Medler Ferro Woodhouse & Mills PLLC

(57) ABSTRACT

Disclosed is a protector capable of stably joining between adjacent bones while providing a proper elasticity thereto. The protector includes an elastic member having a center part which is placed to cover a joint between adjacent bones, and a plurality of fixing members which are located at both end parts of the elastic member and are fixed to the bones.

13 Claims, 9 Drawing Sheets

(51) Int. Cl.
*A61F 2/08* (2006.01)
*A61L 31/14* (2006.01)
*A61B 17/68* (2006.01)
*A61B 17/86* (2006.01)
*A61F 2/00* (2006.01)

(56) References Cited

U.S. PATENT DOCUMENTS

2007/0118130 A1* 5/2007 O'Neil .............. A61B 17/7059
606/279
2013/0023878 A1* 1/2013 Belliard ............. A61B 17/7053
606/74

FOREIGN PATENT DOCUMENTS

| WO | 2005099604 | 10/2005 |
| WO | 2006119216 | 11/2006 |
| WO | 2010040107 | 4/2010 |

OTHER PUBLICATIONS

Written Opinion of the International Searching Authority for related international application No. PCT/KR2014/004598 dated Nov. 20, 2014.
International Preliminary Report on Patentability for related international application No. PCT/KR2014/004598 dated Aug. 30, 2016.

* cited by examiner

PROTECTOR

FIELD OF THE INVENTION

The present invention relates to a protector, and more specifically, to a protector capable of stably joining between adjacent bones while providing a proper elasticity thereto.

BACKGROUND

Commonly, adjacent parts of bones, which were fractured or dislocated by such as an accident, or damaged due to wearing of cartilage or a disc, are fixed or joined by various publicly known means in order to allow the adjacent bones to be joined with each other.

Further, in order to facilitate the treatment and avoid a mechanical stress which causes separation of a bonded part during physical activities, it is necessary to limit movement of the related body or assist the muscles present in the related body part.

As a surgical procedure for joining adjacent bones in the related art, there is a method including the steps of: penetrating holes in an osseous tissue, inserting anchors into the holes, and connecting the anchors with each other by connectors such as a type of bar and plate. Such a surgical operation method may be applied to an osseous tissue such as that in a spine, but it is difficult to operate a soft osseous tissue such as that in an ankle by the above-described method because such an anchor is not stably fixed to the osseous tissue.

In addition, a joint part such as the ankle has a large range of motion due to muscles, however, there is no mechanism to limit the range of motion or aid the motion of muscles. Thereby, a large burden may be applied to the damaged muscle or muscles may be more severely damaged by the burden applied thereto.

See, e.g., Korean Patent Registration No. 10-1042506, incorporated herein by reference.

BRIEF SUMMARY

In some embodiments, the invention is directed to a protector comprising an elastic member having a center part which is placed to cover a joint between adjacent bones; and a plurality of fixing members which are located at both end parts of the elastic member and are fixed to the bones.

In some embodiments, the elastic member is a net knitted by a wire. In some embodiments, the fixing members are attached to nodes of the net. In some embodiments, each mesh of the net has a rhombic shape arranged toward the both end parts of the elastic member. In some embodiments, the elastic member has a different mesh number between a center part and both end parts thereof. In some embodiments, the elastic member is knitted by wires having different elongation between a center part and both end parts thereof.

In some embodiments, the elastic member includes a center part having a center inner part which is located at a center thereof and center outer parts which are connected to both ends of the center inner part and knitted by wires having different elongation from the center inner part. In some embodiments, the elastic member is made of a fabric having elasticity. In some embodiments, the fabric has an elongation direction facing both end parts thereof.

In some embodiments, the elastic member has a hybrid structure in which a center part thereof is made of a fabric having elasticity and both end parts thereof are a net knitted by wires which are connected to the center part. In some embodiments, wherein the fixing members are attached to the nodes of the net. In some embodiments, each mesh of the net has a rhombic shape arranged toward the both end parts of the elastic member.

In some embodiments, the fixing member is an anchor which includes a head part having a head upper plate and a head lower plate which are disposed at an interval to form a space for the elastic member to be inserted therein and fixed thereto, and a body part which is integrally formed with the head part and has wedges formed thereon.

In some embodiments, the fixing member is a screw which includes a head part having a head upper plate and a head lower plate which are disposed at an interval to form a space for the elastic member to be inserted therein and fixed thereto, and a tread part which is integrally formed with the head part and has a spiral formed thereon.

DETAILED DESCRIPTION

Technical Problem

Figure 1:
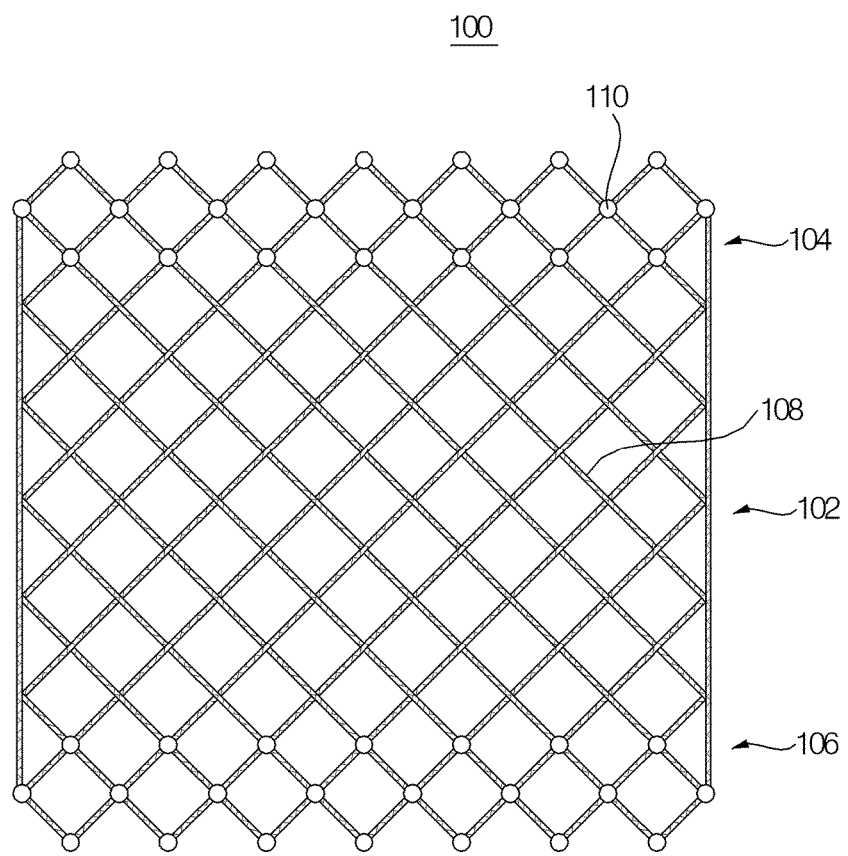
FIG. 1 is a schematic plane view of a protector according to Embodiment 1 of the present invention.

In consideration of the above-described circumstances, it is an object of the present invention to provide a protector capable of stably joining between adjacent bones while providing a proper elasticity thereto.

Technical Solution

In order to accomplish the above objects, there is provided a protector including: an elastic member having a center part which is placed to cover a joint between adjacent bones; and a plurality of fixing members which are located at both end parts of the elastic member and are fixed to the bones. Accordingly, both end parts of the elastic member are fixed to end parts of adjacent bones by the fixing members, and a part between adjacent bones is covered by the elastic member.

The elastic member may be a net knitted by a wire. As a result, the elastic member takes up minimal space, and thereby elasticity may be reliably ensured.

The fixing members may be attached to nodes of the net. Since the fixing members are located at the nodes in which the wires intersect with each other, even if a tensile force is applied to the elastic member by pressing the fixing members, the protector may be placed between the adjacent bones while maintaining the shape of net without twisting thereof.

Each mesh of the net may have a rhombic shape arranged toward the both end parts of the elastic member. As a result, the elastic direction of the net will be determined by the shape of the meshes. Since the mesh has the rhombic shape, the net may be expanded and contracted in a longitudinal direction as well as a width direction.

In addition, the elastic member may have a different mesh number between a center part and both end parts thereof. Alternately, the elastic member may be knitted by wires having different elongation between a center part and both end parts thereof. Since the elongation of the end parts of the bones and the part between adjacent bones are different from each other, in order to correspond the differences in elongation, it is preferable to have a structure in which only the elastic member placed on the part between adjacent bones is formed by a material with an excellent elasticity, while the elastic member placed on the end parts of the bones are formed by a material with a relatively low elasticity for fixing thereof.

The elastic member may include a center part having a center inner part which is located at a center thereof and center outer parts which are connected to both ends of the center inner part and knitted by wires having different elongation from the center inner part.

The elastic member may be made of a fabric having elasticity. The fabric may be used if any problem is generated due to friction, etc., when it is made of a wire, or if it is necessary to isolate the part between bones from other parts. In this case, the fixing members may be inserted into insertion holes formed in the elastic member.

Further, it is preferable that the fabric has an elongation direction facing both end parts thereof so as to correspond a motion of adjacent bones.

The elastic member may have a hybrid structure in which a center part thereof is made of a fabric having elasticity and both end parts thereof are a net knitted by wires which are connected to the center part. In this case, it is preferable that the fixing members are attached to the nodes of the net, as described above. Further, each mesh of the net may have a rhombic shape arranged toward the both end parts of the elastic member so as to previously determine the elongation direction thereof.

The fixing member may be an anchor which includes a head part having a head upper plate and a head lower plate which are disposed at an interval to form a space for the elastic member to be inserted therein and fixed thereto, and a body part which is integrally formed with the head part and has wedges formed thereon. Specifically, since a plurality of fixing members having a small size are used corresponding to the number of the nodes, a shearing force applied to the elastic member is dispersed, and thereby the protector may be used for a region consisting of the soft osseous tissue.

The fixing member may be a screw which includes a head part having a head upper plate and a head lower plate which are disposed at an interval to form a space for the elastic member to be inserted therein and fixed thereto, and a thread part which is integrally formed with the head part and has a spiral formed thereon.

Advantageous Effects

According to the present invention, it is possible to provide a protector capable of stably joining between the adjacent bones while providing a proper elasticity thereto. Therefore, it is possible to reliably protect a surgical site by assisting the muscles present in the jointed part and stabilizing the joints. In particular, the protector of the present invention may be operated on the surgical site such as an ankle, which is a part difficult to fix the screws in the related art.

Exemplary Embodiments

Hereinafter, exemplary embodiments of the present invention will be described in detail with reference to the accompanying drawings. Referring to the drawings, wherein like reference characters designate like or corresponding parts throughout the several views. In the embodiments of the present invention, a detailed description of publicly known functions and configurations that are judged to be able to make the purport of the present invention unnecessarily obscure are omitted.

FIG. 1 illustrates a protector 100 according to Embodiment 1 of the present invention. The protector 100 includes an elastic member having a center part 102 which is placed to cover a joint 12 between adjacent bones, and a plurality of fixing members which are located at both end parts 104 and 106 of the elastic member and are fixed to the bones.

The elastic member has the center part 102 which is placed on a surgical site to schematically cover a joint part, and the both end parts 104 and 106 which are continuously or integrally connected to both sides of the center part 102. Accordingly, the both ends of the elastic member are fixed to both ends 10 and 14 of the adjacent bones by the fixing members, and the joint 12 between the adjacent bones are covered by the elastic member.

The joint 12 mentioned in the present invention means a connecting site between two or more adjacent bones, and includes all of a fixed joint which does not move at all, as well as a semi-movable joint which can slightly move within a small range and a movable joint with an excellent mobility within a large range.

The elastic member may be formed of various publicly known materials harmless to the human body. For example, a biomaterial such as silicone rubber, polyurethane, polyvinyl alcohol hydrogel, polyvinylpyrrolidone, poly HEMA, HYPAN™ and Salubria™ may be used as the material of the elastic member. In Embodiment 1, the elastic member is a net knitted by a wire 108 of the above-described material. A process of knitting the net using the above-described polymer or polymerized polymer is a technique well known in the related art, and therefore, a detailed description thereof will be omitted in this disclosure.

Since the elastic member is the net knitted by the wire 108, the elastic member takes up minimal space, and thereby elasticity may be reliably ensured. Further, the net has an advantage in terms of elasticity due to structural characteristics thereof.

Each mesh of the net has a rhombic shape arranged toward the both end parts of the elastic member as illustrated in FIG. 1. Herein, the elastic direction of the net will be determined by the shape of the meshes. Since the mesh has the rhombic shape, the net may be expanded and contracted in a longitudinal direction as well as a width direction.

In addition, the fixing members are characterized by being attached to nodes of the net. Since the fixing members are located at the nodes in which the wires 108 intersect with each other, even if a tensile force is applied to the elastic member by pressing the fixing members, the protector may be placed at the surgical site between the adjacent bones while maintaining the shape of net without twisting thereof.

Specifically, if the fixing members are previously attached to the nodes during manufacturing the net by the wire 108, it is preferable that a process of locating the fixing members at the respective nodes during a surgical operation may be omitted and dropping of the fixing members into the surgical site may be prevented.

Accordingly, the fixing members, which have a structure capable of previously being attached to the nodes, may use an anchor 110 or a screw 150.

Figure 2A:
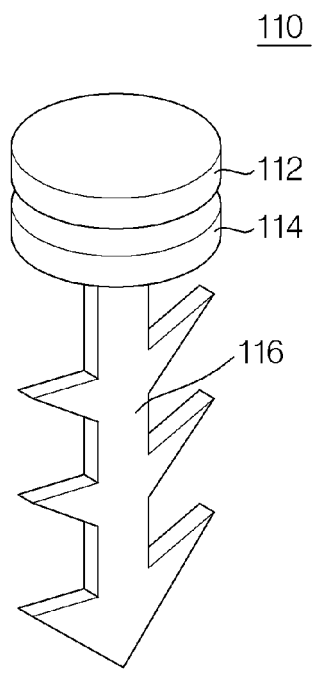
FIGS. 2A to 2C are perspective views of the anchors used in the protector of FIG. 1.

The anchor 110 includes, as illustrated in FIG. 2A, a head part having a head upper plate 112 and a head lower plate 114 which are disposed at an interval to form a space for the elastic member to be inserted therein and fixed thereto, and a body part 116 which is integrally formed with the head part and has wedges formed thereon.

Therefore, the anchors 110, which are previously attached to the nodes of the elastic member, are used in a surgical operation while the nodes of the elastic member are inserted in the space formed between the head upper plate 112 and the head lower plate 114.

Specifically, since a plurality of fixing members having a small size are used corresponding to the number of the nodes, a shear force applied to the elastic member is dispersed, and thereby the protector of the present invention may be used for a region consisting of the soft osseous tissue.

Figure 2B:
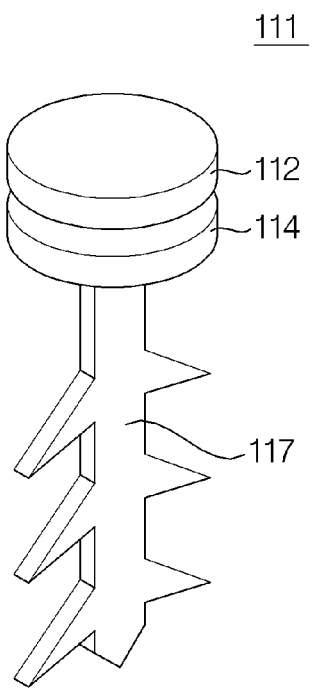

FIG. 2B illustrates another type of an anchor 111. The anchor 111 has a body part 117 on which generally downward facing wedges are formed, unlike the anchor 110 of FIG. 2A.

Figure 2C:
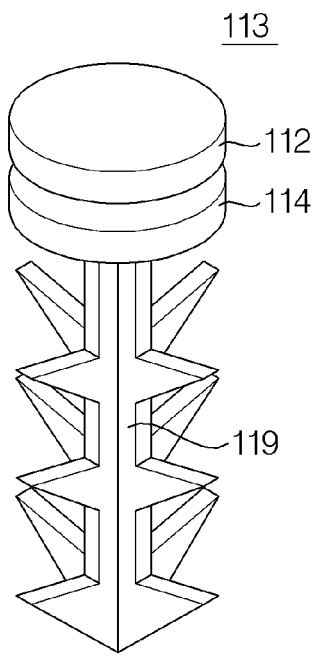
Figure 3:
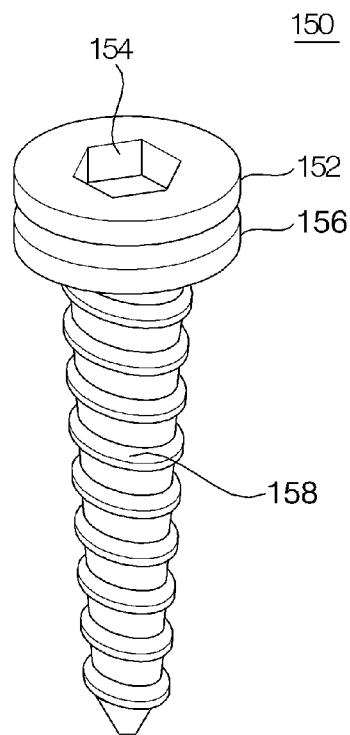
FIG. 3 is a perspective view of a screw used in the protector of FIG. 1.

FIG. 2C illustrates another type of an anchor 113. The anchor 113 has a body part 119 on which wedges are formed so as to have a substantial cross shape as seen from a bottom, unlike the anchor 110 of FIG. 2A.

In addition, the screw 150, which is another type of the fixing members, includes a head part having a head upper plate 152 and a head lower plate 156 which are disposed at an interval to form a space for the elastic member to be inserted therein and fixed thereto, and a thread part 158 which is integrally formed with the head part and has a spiral formed thereon. The upper plate 152 has an insertion groove 154 in which a fastening tool such as a wrench can be inserted.

The fixing members may be made of a material harmless to the human body such as a titanium alloy.

Figure 4:
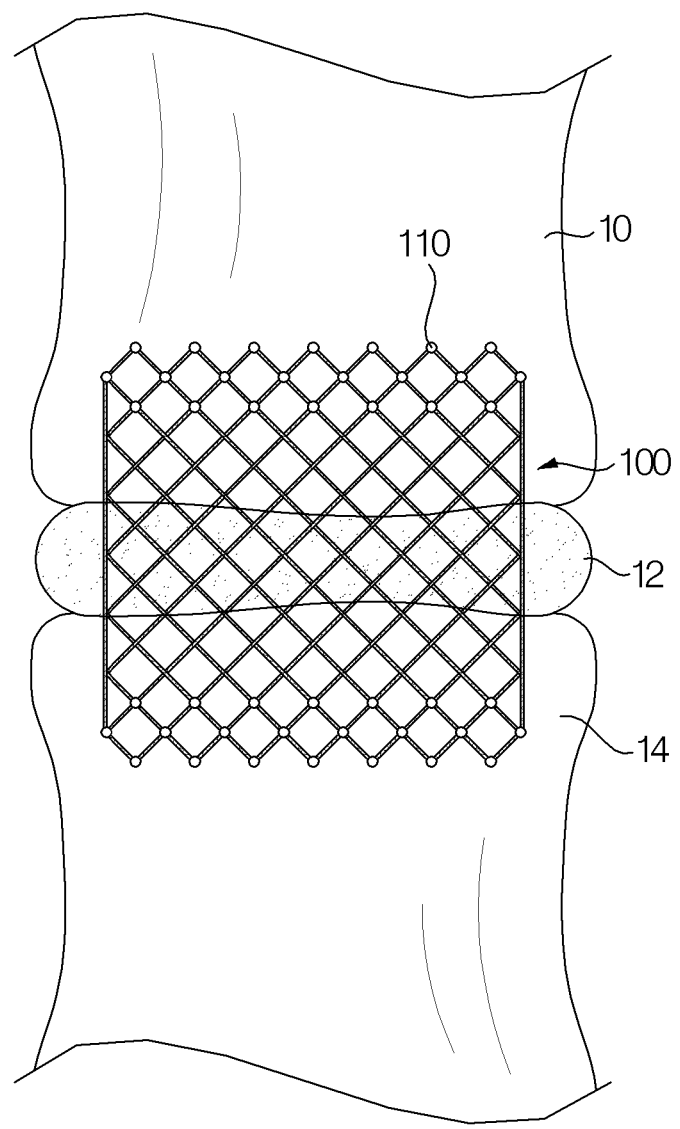
FIG. 4 is a schematic plane view illustrating a state in which the protector of FIG. 1 is placed on adjacent bones.

The protector 100 according to Embodiment 1 of the present invention basically has the above-described configuration. Hereinafter, a placed state of the protector 100 will be described with reference to FIG. 4.

First, the protector 100 is positioned on the joint part to be protected. At this time, the protector 100 is placed on a surgical site, so that the center part 102 thereof covers the joint 12 and both end parts 104 and 106 are positioned at both ends 10 and 14 of the bones.

In this state, one of the fixing members near to the center part 102 is firstly fixed to both ends 10 and 14 of the bones. At this time, the fixing members are fixed in such a manner that one of the fixing members positioned on one side of the both end parts 104 and 106 is fixed, and then one of the fixing members positioned on the other side thereof is fixed. Thus, the elastic member is maintained in a state of applying the tension thereto.

Then, another fixing member which is positioned on an outside from the previously located fixing member with respect to the center part 102 is fixed to both ends of the bones, thereby the protector 100 is placed in a state of maintaining a constant tension applied thereto. Specifically, it is possible to fix the fixing members by pulling the elastic member in the longitudinal direction as well as the width direction thereof as necessary.

Figure 5:
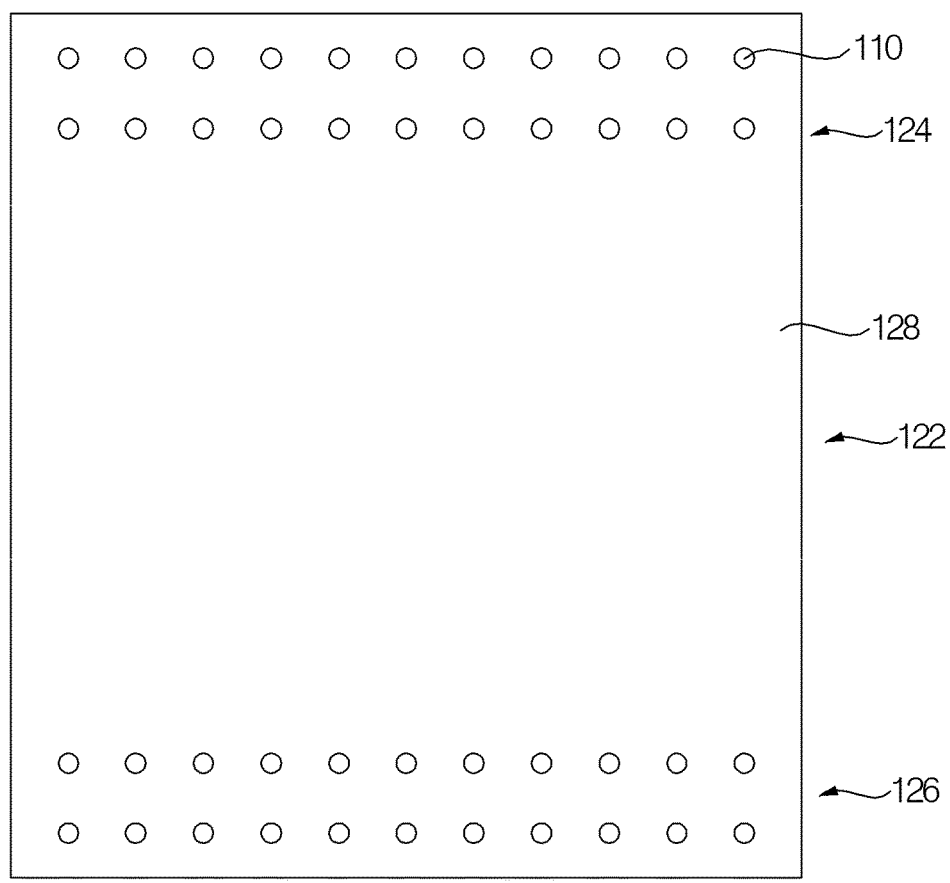
FIG. 5 is a schematic plane view of a protector according to Embodiment 2 of the present invention.

Next, a protector 120 according to Embodiment 2 of the present invention will be described with reference to FIG. 5. The protector 120 is characterized in that the elastic member is made of a fabric 128. A center part 122 and both end parts 124 and 126 of the elastic member are formed by one fabric 128, and anchors 110 of fixing members are previously located in penetrated holes which are formed at both sides of the fabric 128. The placing process of the protector 120 is the same as that of the protector 100 according to Embodiment 1, except that the fabric 128 is required to be carefully placed so as not to form wrinkles thereon. The protector 120 may be used if any problem is generated due to friction, etc., when it is made of a wire, or if it is necessary to isolate a part between bones from other parts.

Figure 6:
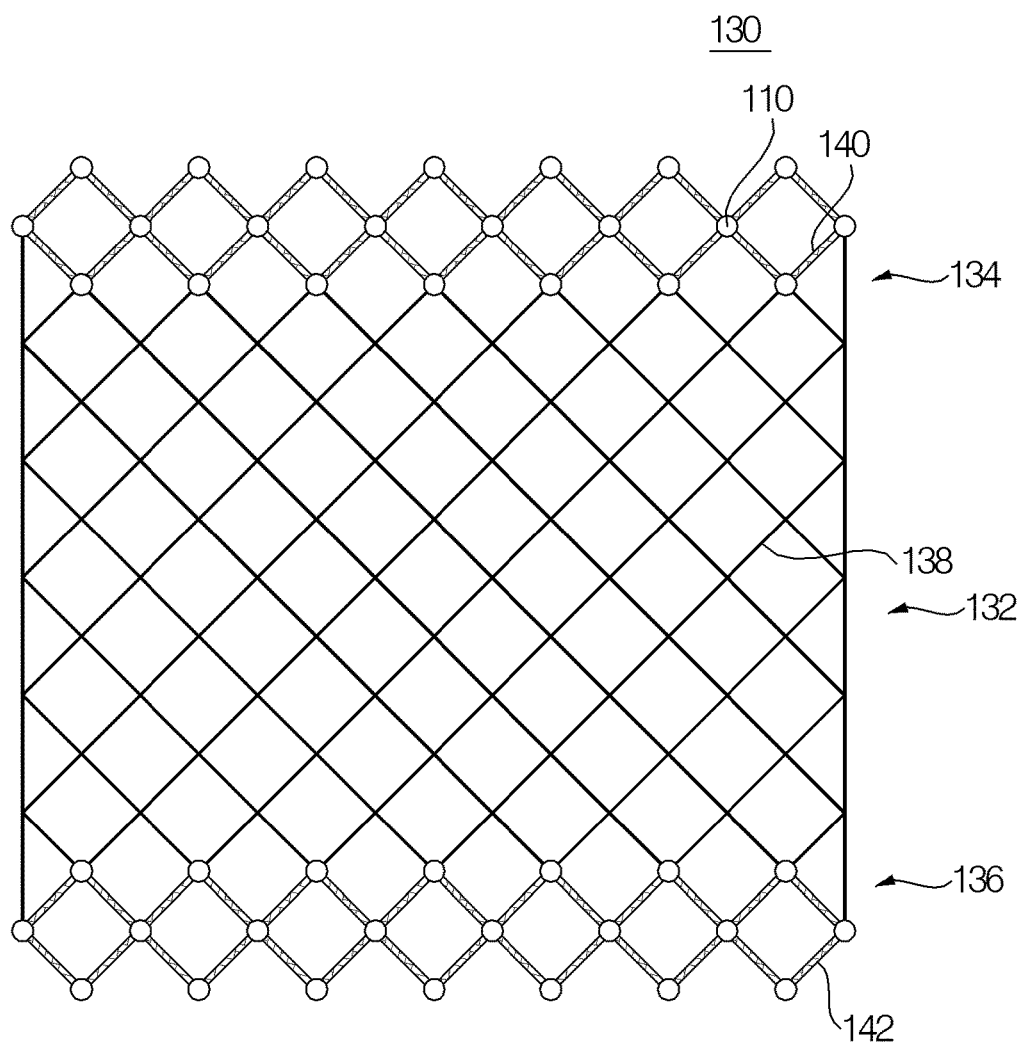
FIG. 6 is a schematic plane view of a protector according to Embodiment 3 of the present invention.

In addition, a protector 130 according to Embodiment 3 of the present invention will be described with reference to FIG. 6. The protector 130 is characterized in that the elastic member is a net knitted by a wire 138 forming a center part 132 and wires 140 and 142 forming both end parts 134 and 136, which have elongation different from each other, unlike the protector 100 of Embodiment 1.

The wires 138, 140 and 142 may have elongation different from each other by using a method of varying a thickness or material thereof. Due to differences in elongation, an extension amount of the center part 132 may be different from that of the both end parts 134 and 136. The protector according to this embodiment may be used if it is necessary to increase the extension amount of the center part 132 due to a large momentum of the joint part.

Figure 7:
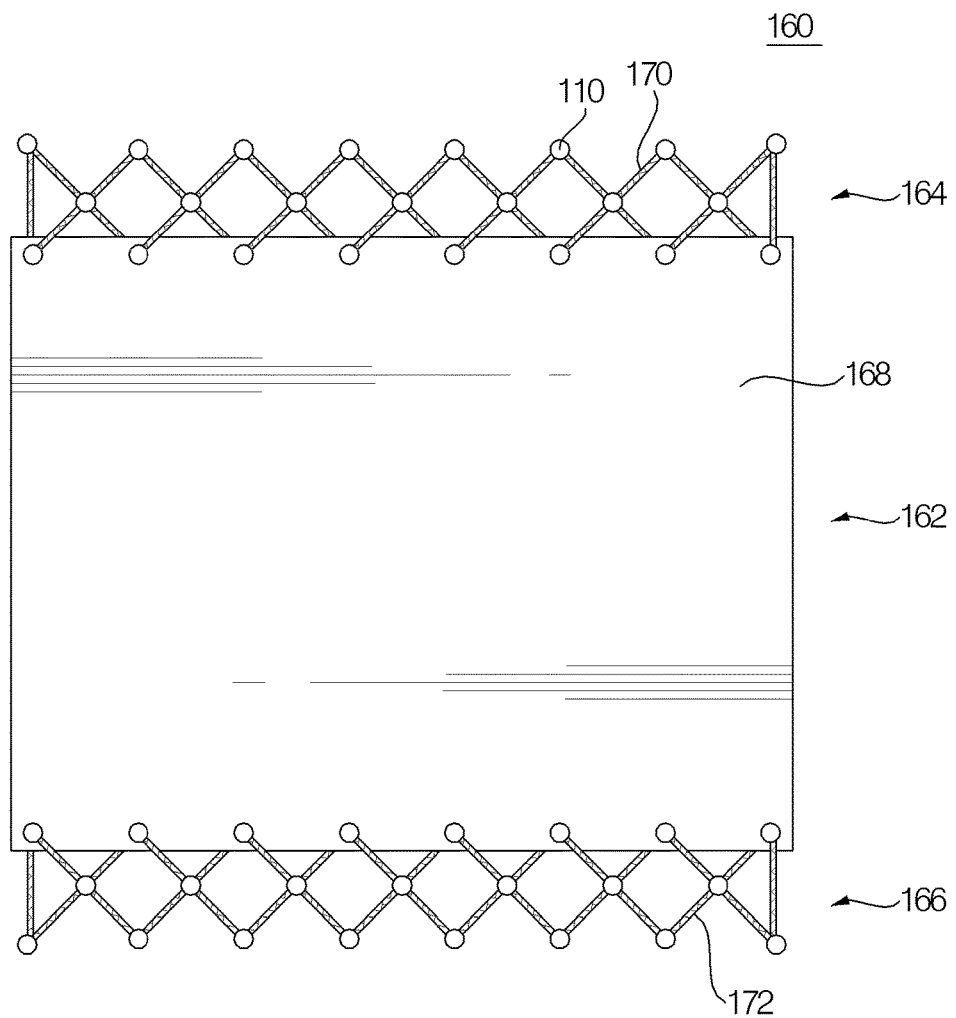
FIG. 7 is a schematic plane view of a protector according to Embodiment 4 of the present invention.

Further, a protector 160 according to Embodiment 4 of the present invention will be described with reference to FIG. 7. The protector 160 is characterized in that the elastic member has a hybrid structure in which a center part 162 thereof is made of a fabric having elasticity and both end parts 164 and 166 thereof are a net knitted by wires 170 and 172 which are connected to the center part 162. That is, the protector having the hybrid structure combined the protector of Embodiment 1 with the protector of Embodiment 2, so that only the joint part is covered by the fabric. In this case, as described above, it is preferable that the anchors 110 of the fixing members are attached to nodes of the net, as described above. Further, the elastic direction of the net may be previously be determined by forming each mesh of the net in a rhombic shape arranged toward the both end parts of the elastic member.

Figure 8:
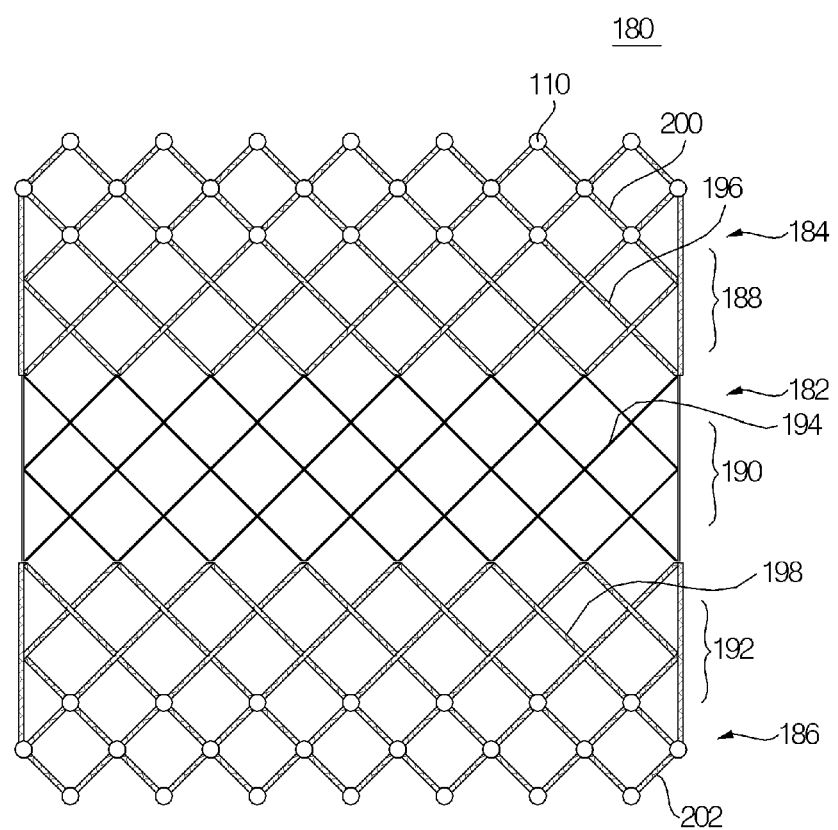
FIG. 8 is a schematic plane view of a protector according to Embodiment 5 of the present invention.

Further, a protector 180 according to Embodiment 5 of the present invention will be described with reference to FIG. 8. The protector 180 is characterized in that the elastic member has a net which includes: a center part 182 having a center inner part 190 which is located at a center thereof and center outer parts 188 and 192 which are connected to both ends of the center inner part 190, wherein the center inner part 190 and the center outer parts 188 and 192 are knitted by wires 194, and 196 and 198, which have elongation different from each other; and both end parts 184 and 186 which are connected to both sides of the center part 182 and knitted by wires 200 and 202 which may have elongation the same as or different from the wires 194, and 196 and 198 forming the center part 182. In Embodiment 5, the wires 196 and 198 forming the center outer part 188 and 192 and the wires 200 and 202 forming the both end parts 184 and 186 have the same elongation as each other. The protector 180 may be used if the joint part has a large articular capsule such as a movable joint.

Figure 9:
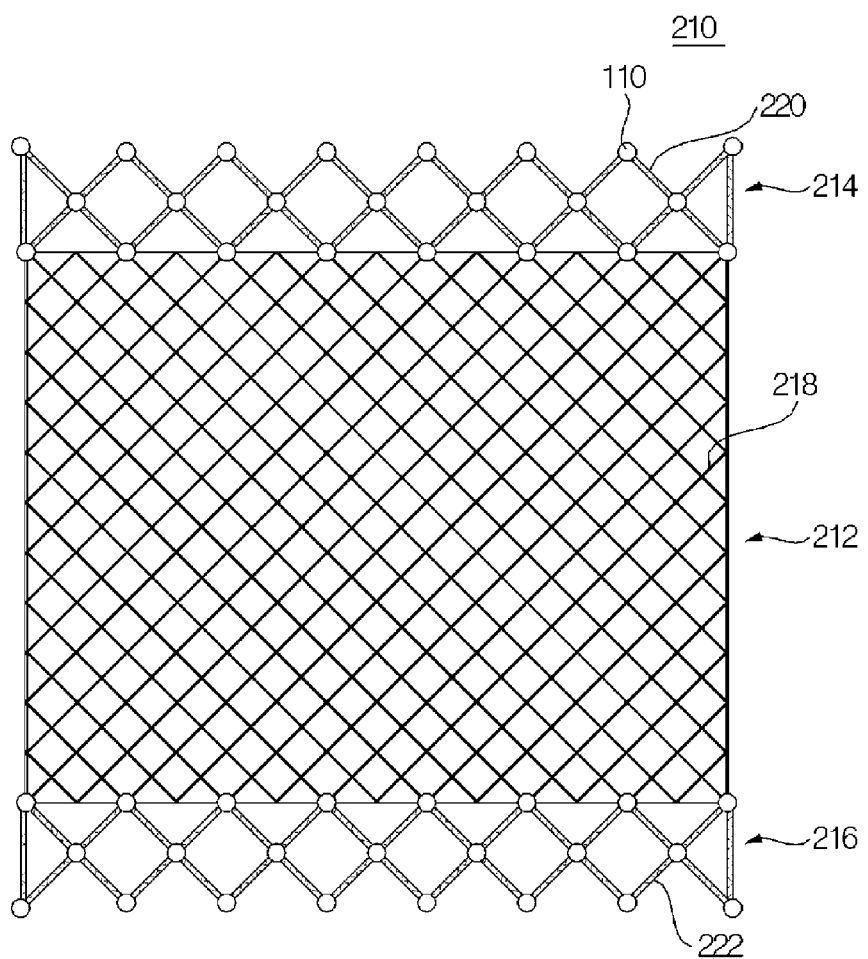
FIG. 9 is a schematic plane view of a protector according to Embodiment 6 of the present invention.

Furthermore, a protector 210 according to Embodiment 6 of the present invention will be described with reference to FIG. 9. The protector 210 is characterized in that the elastic member has a different mesh number between a center part 212 and both end parts 214 and 216 thereof. Therefore, even if the elastic member is formed by wires of the same material, the elongation of the center part 212 and the both end parts 214 and 216 are different from each other. Further, in FIG. 9, the elastic member is configured in such a manner that a wire 218 forming the center part 212; and wires 220 and 222 forming the both end parts 214 and 216 have elongation different from each other. Therefore, it is possible to more greatly increase the difference in extension amount between the center part 212 and the both end parts 214 and 216, compared to the protector 130 of the Embodiment 3.

While the present invention has been described with reference to the preferred embodiments, the present invention is not limited to the above-described embodiments, and it will be understood by those skilled in the related art that various modifications and variations may be made therein without departing from the scope of the present invention as defined by the appended claims.

DESCRIPTION OF REFERENCE NUMERALS 10, 14: end of bone
12: joint
100, 120, 130, 160, 180, 210: protector
102, 122, 132, 162, 182, 212: center part
104, 106, 124, 126, 134, 136, 164, 166, 184, 186, 214, 216: both end parts
108, 138, 170, 172, 194, 196, 198, 200, 202, 208, 220, 222: wire
110: anchor
112, 152: head upper plate
114, 156: head lower plate
116: body part
128, 168: fabric
154: insertion groove
158: thread part
150: screw
188, 192: center outer part
190: center inner part

What is claimed is:

1. A protector comprising:
an elastic member having a center part which is configured to be placed to cover a joint between adjacent bones; and
a plurality of fixing members which are located at both end parts of the elastic member and are capable of being fixed to the bones,
wherein at least one of plurality of fixing members is an anchor which includes a head part having a head upper placed and a head lower plate which are disposed at an interval to form a space for the elastic member to be inserted therein and fixed thereto, and a body part which is integrally formed with the head part and has wedges formed thereon.

2. The protector according to claim 1, wherein the elastic member is a net knitted by a wire.

3. The protector according to claim 2, wherein the fixing members are attached to nodes of the net.

4. The protector according to claim 2, wherein a mesh of the net has a rhombic shape arranged toward the both end parts of the elastic member.

5. The protector according to claim 2, wherein the elastic member has a different mesh number between a center part and both end parts thereof.

6. The protector according to claim 2, wherein the elastic member is knitted by wires having different elongation between a center part and both end parts thereof.

7. The protector according to claim 2, wherein the elastic member includes a center part having a center inner part which is located at a center thereof and center outer parts which are connected to both ends of the center inner part and wherein the elastic member is knitted by wires having different elongation from the center inner part.

8. The protector according to claim 1, wherein the elastic member is made of a fabric having elasticity.

9. The protector according to claim 8, wherein the fabric has an elongation direction facing both end parts thereof.

10. The protector according to claim 1, wherein the elastic member has a hybrid structure in which a center part thereof is made of a fabric having elasticity and both end parts thereof are a net knitted by wires which are connected to the center part.

11. The protector according to claim 10, wherein the fixing members are attached to nodes of the net.

12. The protector according to claim 10, wherein a mesh of the net has a rhombic shape arranged toward the both end parts of the elastic member.

13. A protector comprising:
an elastic member having a center part which is configured to be placed to cover between adjacent bones; and
a plurality of fixing members which are located at both end parts of the elastic member and are capable of being fixed to the bones,
wherein at least one of the plurality of fixing members is an anchor or a screw which includes a head part having a head upper plate and a head lower place which are disposed at an interval to form a space for the elastic member to be inserted therein and fixed thereto, and a tread part which is integrally formed with the head part and has a spiral formed thereon.

* * * * *